United States Patent
Towse et al.

(10) Patent No.: US 8,221,639 B2
(45) Date of Patent: Jul. 17, 2012

(54) SURFACE TREATMENT METHODS FOR IMPLANTS MADE OF TITANIUM OR TITANIUM ALLOY

(75) Inventors: Ross Williams Towse, Palm City, FL (US); Robert Leslie Mayfield, Jupiter, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 1515 days.

(21) Appl. No.: 11/361,286

(22) Filed: Feb. 23, 2006

(65) Prior Publication Data

US 2006/0219661 A1 Oct. 5, 2006

Related U.S. Application Data

(60) Provisional application No. 60/656,131, filed on Feb. 24, 2005.

(51) Int. Cl.
*C03C 15/00* (2006.01)
(52) U.S. Cl. ............... 216/83; 252/79; 216/53; 216/89; 623/11.11; 623/53
(58) Field of Classification Search .............. 252/79; 216/53, 89; 623/11.11, 23, 53
See application file for complete search history.

(56) References Cited

U.S. PATENT DOCUMENTS

| | | | |
|---|---|---|---|
| 2,981,610 A | 4/1961 | Snyder et al. | |
| 3,468,774 A | 9/1969 | Kendall | |
| 4,195,409 A | 4/1980 | Child | |
| 4,336,618 A | 6/1982 | Raab | |
| 4,818,559 A | 4/1989 | Hama et al. | |
| 4,826,434 A | 5/1989 | Kruger | |
| 4,846,897 A * | 7/1989 | Nakagawa et al. | 148/251 |
| 4,871,578 A | 10/1989 | Adam et al. | |
| 4,874,434 A | 10/1989 | Riggs, Jr. | |
| 5,344,457 A | 9/1994 | Pilliar et al. | |
| 5,360,448 A | 11/1994 | Thramann | |
| 5,456,723 A | 10/1995 | Steinemann et al. | |
| 5,484,286 A | 1/1996 | Hansson | |
| 5,571,017 A | 11/1996 | Niznick | |
| 5,571,188 A | 11/1996 | Ellingsen et al. | |
| 5,588,838 A | 12/1996 | Hansson et al. | |
| 5,603,338 A | 2/1997 | Beaty | |
| 5,863,201 A | 1/1999 | Lazzara et al. | |
| 5,876,453 A | 3/1999 | Beaty | |

(Continued)

FOREIGN PATENT DOCUMENTS

EP 1477141 * 5/2004

(Continued)

OTHER PUBLICATIONS

English Translation of Japanese Patent Application No. 3-146679 (8 pages).

(Continued)

*Primary Examiner* — Nadine Norton
*Assistant Examiner* — Maki Angadi
(74) *Attorney, Agent, or Firm* — Nixon Peabody LLP

(57) ABSTRACT

A method of producing a generally uniformly roughened surface on Ti 6/4 alloy or titanium for contact with living bone comprises exposing the Ti 6/4 alloy or titanium in an aqueous solution of citric acid and hydrofluoric acid for a suitable time period to remove the native oxide from the Ti 6/4 alloy or titanium so as to expose the Ti 6/4 or titanium metal surface and create the desired surface topography.

20 Claims, 25 Drawing Sheets

U.S. PATENT DOCUMENTS

| | | | |
|---|---|---|---|
| 6,069,295 | A | 5/2000 | Leitao |
| 6,491,723 | B1 | 12/2002 | Beaty |
| 6,527,938 | B2 | 3/2003 | Bales et al. |
| 6,652,765 | B1 | 11/2003 | Beaty |
| 6,969,474 | B2 | 11/2005 | Beaty |
| 2002/0198601 | A1* | 12/2002 | Bales et al. ............ 623/23.55 |
| 2004/0167632 | A1 | 8/2004 | Wen et al. |

FOREIGN PATENT DOCUMENTS

| | | |
|---|---|---|
| EP | 1449544 | 8/2004 |
| EP | 1477141 | 11/2004 |
| JP | 58-147561 | 2/1982 |
| JP | 60-056077 | 9/1983 |
| JP | 3-146679 | 6/1991 |
| WO | WO 9517217 | 6/1995 |
| WO | WO 0207792 | 1/2002 |
| WO | WO 2004008983 | 1/2004 |

OTHER PUBLICATIONS

"The Influence of Various Titanium Surfaces on the Interface Strength Between Implants and Bone", *Advances in Biomaterials*, vol. 9, pp. 309-314, Elsevier Science Publishers BV, Amsterdam 1990.

PCT International Search Report for International Application No. PCT/US06/06082 dated Dec. 1, 2006 (2 pages).

PCT Written Opinion for International Application No. PCT/US06/06082 dated Dec. 1, 2006 (3 pages).

Search Report and Written Opinion for European Application No. 06735650.1 dated Aug. 20, 2009 (11 pages).

* cited by examiner

SURFACE TREATMENT METHODS FOR IMPLANTS MADE OF TITANIUM OR TITANIUM ALLOY

CROSS-REFERENCE WITH RELATED APPLICATION

This application claims the benefit of the U.S. Provisional Application 60/656,131, filed on Feb. 24, 2005, and entitled "Surface Treatment Methods For Implants Made Of Titanium Or Titanium Alloy" and this provisional application is hereby incorporated by reference in its entirety.

FIELD OF INVENTION

This present invention relates to methods of producing a surface using titanium 6/4 alloy or titanium and, more specifically, to methods of producing a surface of an implant such as a dental implant using titanium 6/4 alloy or titanium that improves the osseointegration of the implant surface with the bone.

BACKGROUND OF THE INVENTION

It is known to roughen the surface of implants. Various approaches have been suggested, each producing a unique surface. One approach has been to apply materials to the surface of the implant such as, for example hydroxyapitite, a material that is considered also to improve the bonding of the implant to bone because the hydroxyapitite is chemically related to bone. In a related approach, titanium particles have been sprayed onto a titanium implant to roughen the surface. Roughening can also be done by removing some of the surface. Grit blasting with fine particles has been proposed to create dents and to abrade away some of the surface.

Another method is the use of acid etching to create a roughened surface. At least one supplier of dental implants has proposed grit blasting to create a coarse roughened surface, followed by acid etching to form a superimposed fine roughening. In a series of U.S. patents, including U.S. Pat. Nos. 5,603,338, 5,876,453, 5,863,201, assigned to Implant Innovations Inc., a unique two-step acid treatment was disclosed and is used on dental implants having an Osseotite® surface. The first acid treatment used aqueous hydrofluoric acid to remove the "native oxide", which is the titanium oxide found on titanium metal surfaces. Removing the native oxide is important since it makes the metal surface more easily accessible to etching by other acids that are otherwise unable to uniformly etch the surface of titanium containing native oxide. The second acid treatment desirably used a mixture of hydrochloric and sulfuric acids to etch the exposed titanium surface. A relatively fine etching was achieved, having peak-to-valley heights of 10 microns or less. The peak-to-peak distance typically is about from about 1 to about 3 microns. This Osseotite® surface has achieved commercial success, having reduced the time required for osseointegration of the titanium implant with bone.

Previous U.S. patents have shown the titanium surface obtained by scanning electron microscopy (SEM). Another method of describing the surface is surface mapping microscopy (SMM), which produces a computer-generated three-dimensional picture of the region being examined, and several calculated measures of the roughness of the surface. It will be understood by those skilled in the art that acid treatment produces a surface that appears very uniform to the naked eye, but contains variations that become evident only when greatly magnified, as in the photomicrographs. Each region will not be precisely the same as the others, but nevertheless, the variations are small and fall within the general limits discussed above. By carefully controlling the treatment process, each implant has substantially the same surface.

It would be desirable to improve and simplify existing processes, while still producing a desirable uniform surface.

SUMMARY OF INVENTION

According to one method, a generally uniformly roughened surface on Ti 6/4 alloy for contact with living bone is produced. The Ti 6/4 alloy is exposed in an aqueous solution of citric acid and hydrofluoric acid for a suitable time period to remove the native oxide from the Ti 6/4 alloy so as to expose the Ti 6/4 metal surface and create the desired surface topography.

According to another method, a generally uniformly roughened surface on Ti 6/4 alloy for contact with living bone is produced. The Ti 6/4 alloy is exposed to an aqueous solution of citric acid and hydrofluoric acid for a suitable time period to remove the native oxide from the Ti 6/4 alloy so as to expose the Ti 6/4 metal surface and etch the exposed metal to achieve a roughened surface having irregularities with peak-to-valley heights of less than about 10 microns.

According to a further method, a surface of a Ti 6/4 alloy implant that is surgically implantable in living bone is prepared. The surface has a native oxide layer thereon. The Ti 6/4 alloy is exposed to an aqueous solution of citric acid and hydrofluoric acid for a suitable time period. The aqueous solution of citric acid and hydrofluoric acid removes substantially all of the native oxide from the Ti 6/4 alloy and forms a modified surface with substantially uniform array of irregularities having peak-to-valley heights less than about 10 microns.

According to yet another method, a generally uniformly roughened surface on Ti 6/4 alloy for contact with living bone is produced. An initial treatment is performed that removes substantially all of the native oxide from the surface of the Ti 6/4 alloy. After performing the initial treatment, the Ti 6/4 alloy is exposed in an aqueous solution of citric acid and hydrofluoric acid for a suitable time period to create the desired surface topography.

According to yet a further method, a generally uniformly roughened surface on Ti 6/4 alloy for contact with living bone is produced. An initial treatment is performed that removes substantially all of the native oxide from the surface of the Ti 6/4 alloy. After performing the initial treatment, the Ti 6/4 alloy is exposed to an aqueous solution of citric acid and hydrofluoric acid for a suitable time period to achieve a roughened surface having irregularities with peak-to-valley heights of less than about 10 microns.

According to another method, a surface of a Ti 6/4 alloy implant that is surgically implantable in living bone is prepared. The surface has a native oxide layer thereon. An initial treatment is performed that removes substantially all of the native oxide from the surface of the Ti 6/4 alloy. After performing the initial treatment, the Ti 6/4 alloy is exposed to an aqueous solution of citric acid and hydrofluoric acid for a suitable time period to achieve a roughened surface having irregularities with peak-to-valley heights of less than about 10 microns.

According to one method, a generally uniformly roughened surface on titanium for contact with living bone is produced. The titanium is exposed in an aqueous solution of citric acid and hydrofluoric acid for a suitable time period to remove the native oxide from the titanium so as to expose the titanium surface and create the desired surface topography.

According to another method, a generally uniformly roughened surface on titanium for contact with living bone is produced. The titanium is exposed to an aqueous solution of citric acid and hydrofluoric acid for a suitable time period to remove the native oxide from the titanium so as to expose the titanium metal surface and etch the exposed metal to achieve a roughened surface having irregularities with peak-to-valley heights of less than about 10 microns.

According to a further method, a surface of a titanium implant that is surgically implantable in living bone is prepared. The titanium is exposed to an aqueous solution of citric acid and hydrofluoric acid for a suitable time period. The aqueous solution of citric acid and hydrofluoric acid removes substantially all of the native oxide from the titanium and forms a modified surface with substantially uniform array of irregularities having peak-to-valley heights less than about 10 microns.

According to yet another method, a generally uniformly roughened surface on titanium for contact with living bone is produced. An initial treatment is performed that removes substantially all of the native oxide from the surface of the titanium. After performing the initial treatment, the titanium is exposed in an aqueous solution of citric acid and hydrofluoric acid for a suitable time period to create the desired surface topography.

According to yet a further method, a generally uniformly roughened surface on titanium for contact with living bone is produced. An initial treatment is performed that removes substantially all of the native oxide from the surface of the titanium. After performing the initial treatment, the titanium is exposed to an aqueous solution of citric acid and hydrofluoric acid for a suitable time period to achieve a roughened surface having irregularities with peak-to-valley heights of less than about 10 microns.

According to another method, a surface of a titanium implant that is surgically implantable in living bone is prepared. The surface has a native oxide layer thereon. An initial treatment is performed that removes substantially all of the native oxide from the surface of the titanium. After performing the initial treatment, exposing the titanium to an aqueous solution of citric acid and hydrofluoric acid for a suitable time period to achieve a roughened surface having irregularities with peak-to-valley heights of less than about 10 microns.

DETAILED DESCRIPTION OF THE PREFERRED EMBODIMENTS

Titanium Alloys

Figure 1:
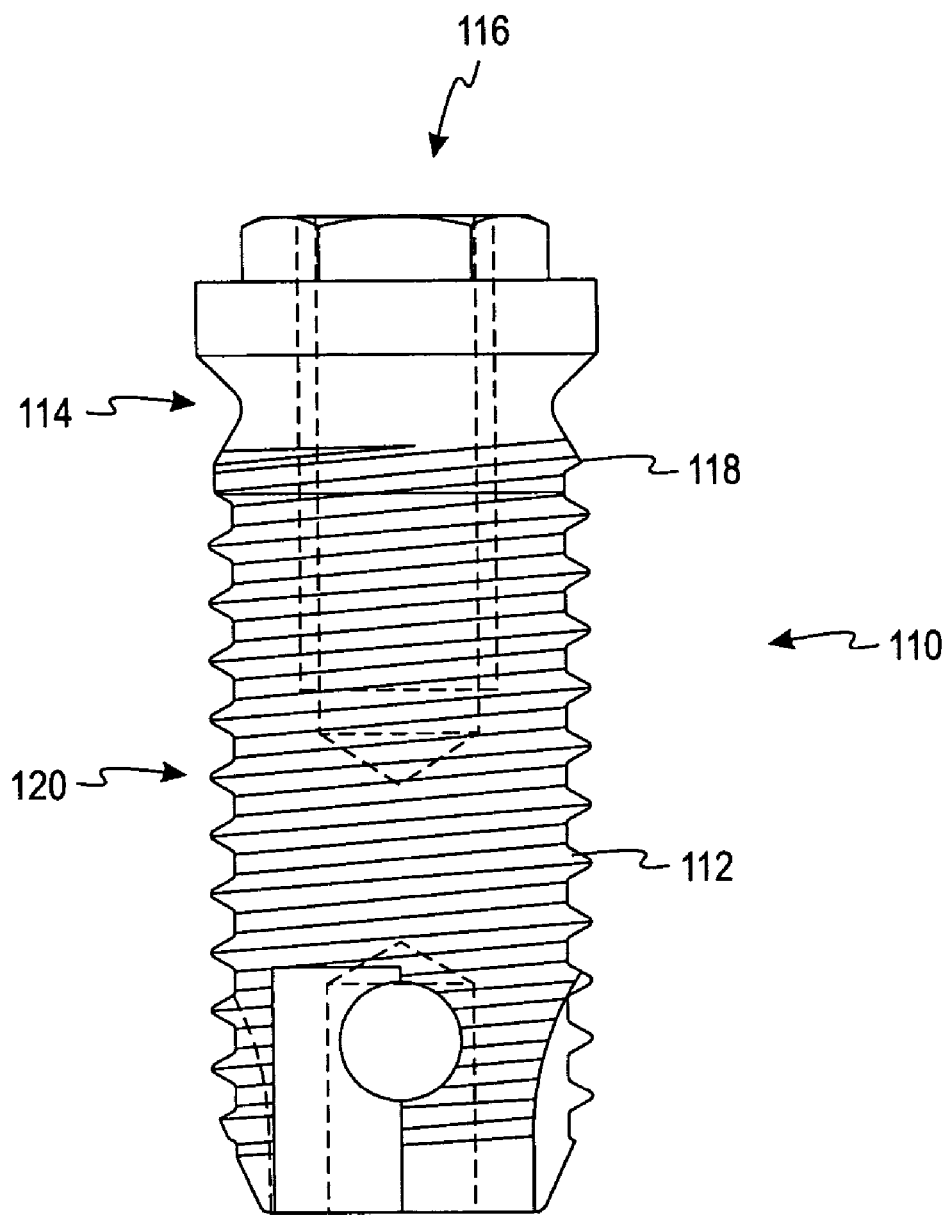
FIG. 1 is a front plan view of a dental implant according to one embodiment.

Titanium alloys have been used in implants such as, for example, dental implants and are typically stronger than the commercially pure grades of titanium. One commonly used titanium alloy, Ti/6Al/4V, generally contains about 6 wt. % aluminum and about 4 wt. % vanadium, hereafter referred to herein as Ti 6/4. One example of a Ti 6/4 alloy that may be used is Ti 6/4 alloy E.L.I. (extra low interstitial). Ti 6/4 alloy E.L.I. is generally referred to as a controlled chemistry version of the standard 6-4 product with lower oxygen content. The aluminum and vanadium content of Ti 6/4 alloy may vary from exactly 6 wt. % aluminum and 4 wt. % vanadium. For example, the Ti 6/4 alloy may comprise from about 5.5 to about 6.5 wt. % aluminum and from about 3.5 to about 4.5 wt. % vanadium.

Ti 6/4 alloys may have other ingredients that are typically present in trace amounts including, but not limited to, nitrogen, carbon, hydrogen, iron and oxygen. Each of these trace amounts is generally less than 1 wt. % and, more specifically, less than 0.5 or 0.25 wt. %. For example, a Ti 6/4 E.L.I. alloy comprises less than 0.08 wt. % oxygen, less than 0.0125 wt. % hydrogen, less than 0.25 wt. % iron, and less than 0.13 wt. % oxygen. It is contemplated that other Ti 6/4 alloys may be used other than Ti 6/4 E.L.I. alloy.

One desirable characteristic of titanium alloys is the rapid formation of tenacious titanium oxide films on the surface, which contributes to titanium's resistance to corrosion. This oxide film is believed to be a combination of various oxides of titanium, including TiO, $TiO_2$, $Ti_2O_3$, and $Ti_3O_4$. This oxide film is referred to as "native oxide" film.

According to one method, a uniformly roughened surface may be obtained on a Ti 6/4 alloy, which is to contact living bone. One method for obtaining such a uniform roughened surface may be performed in a single step. This method involves exposing the Ti 6/4 alloy in an aqueous solution of citric acid and hydrofluoric (HF) acid for a suitable time period to remove the native oxide from the Ti 6/4 alloy so as to expose the Ti 6/4 metal surface and create the desired surface topography.

It is desirable to remove substantially all of the native oxide and even more desirable to remove all of the native oxide from the Ti 6/4 alloy during the exposure to the aqueous solution. It is understood by those of ordinary skill in the art, however, that some smaller bits of native oxide may still remain on the Ti 6/4 alloy after exposure to the citric acid and HF acid. The method typically also includes rinsing the desired surface topography so as to remove the residual aqueous solution.

The aqueous solution generally comprises from about 1 to about 50 wt. % citric acid. More specifically, the aqueous solution comprises from about 16.0 to about 17.3 wt. % citric acid. Citric acid has a formula of $C_6H_8O_7$—$H_2O$ and may be obtained commercially from a variety of sources. For example, citric acid may be obtained from chemical supply houses such as Cole-Parmer Instrument Company or Fisher Scientific, International. The use of citric acid is desirable because it is non-toxic. By using citric acid, it eliminates or reduces the use of more hazardous chemical in the aqueous solution.

The aqueous solution generally comprises from about 0.1 to about 1.0 wt. % HF acid. More specifically, the aqueous solution comprises from about 0.16 to about 0.20 wt. % hydrofluoric acid. Commercially available hydrofluoric acid may be used in the invention.

The aqueous solution may comprise from about 1 to about 50 wt. % citric acid and from about 0.1 to about 1.0 wt. % HF acid. More specifically, the aqueous solution comprises from about 16.0 to about 17.3 wt. % citric acid and from about 0.16 to about 0.20 wt. % HF acid.

The processing conditions for exposing the Ti 6/4 alloy in the aqueous solution of citric acid and HF acid may vary. One non-limiting example of processing conditions for exposing the Ti 6/4 alloy in the aqueous solution of citric acid and HF acid is at a temperature of from about 20 to about 35° C. for a time period of from about 17 to about 20 minutes. One specific example is a temperature of about 30° C. and a time period of from about 18 to about 19 minutes. It is contemplated that other temperatures and times may be used for exposing the aqueous solution of citric acid and HF acid to the Ti 6/4 alloy.

In one embodiment, the one step process of exposing the Ti 6/4 alloy in an aqueous solution of citric acid and HF acid for a suitable time period results in a generally uniform roughened surface having irregularities with peak-to-valley heights of less than about 10 microns. The peak-to-valley heights are measured from the top of the peak to the bottom of the valley. More specifically, the roughened surface has irregularities with peak-to-valley heights of less than about 5 or less than about 3 microns. In one embodiment, the roughened surface generally has irregularities with peak-to-peak distances of from about 1 to about 3 microns. The irregularities may be cone-shaped elements and it is contemplated that such irregularities may be of different shapes. It is contemplated that the irregularities may be in the form of a substantially uniform array.

As mentioned above, the method for preparing a uniformly roughened surface may be done on an implant (e.g., a dental implant), which is surgically implanted in living bone. One non-limiting example of a dental implant (a screw-type dental implant) is depicted in FIG. 1. A generally cylindrical implant 110 of FIG. 1 includes a bone-interfacing surface 112. The bone-interfacing surface 112 typically includes the entire implant surface beyond a narrow collar region 114 on a side wall of the implant 110 at a gingival end 116 thereof. This narrow collar region 114 desirably includes a first turn 118 of the threaded portion 120 of the implant 110. According to one method, the gingival end 116 and the narrow collar region 114 are not etched because these portions of the implant are normally fabricated with precise dimensions to match abutting components that are eventually attached to the gingival end 116 of the implant 110. Additionally, to minimize the risk of infection, it may be desirable to have a smooth surface on that portion of a dental implant that is not embedded in the bone. It is contemplated, however, that the gingival end and/or the narrow collar region may be etched.

It is important to remove substantially all the native oxide from the implant surface (e.g., a dental implant surface) that is intended to interface with the living bone so that a substantially uniform surface texture is formed that promotes uniform bonding to the living bone. Thus, the native oxide layer is desirably removed from substantially all of the entire bone-interfacing surface of the implant.

One method comprises exposing the bone-interfacing portion to an aqueous solution of citric acid and HF acid for a suitable time period. The aqueous solution of citric acid and HF acid removes substantially all of the native oxide from the Ti 6/4 alloy and forms a modified surface. The modified surface generally has irregularities with peak-to-valley heights of less than about 10 microns.

According to another method, the modified surface may be located only on a portion of the plurality of turns of the thread. In another method, the modified surface may be located only below a first turn of the plurality of turns that is adjacent to the gingival end. In yet another embodiment, the aqueous solution of citric acid and HF acid may be exposed to the gingival end.

Another method of preparing a dental implant involves using a blank of a Ti 6/4 alloy. The blank is machined to produce a desired structure of the dental implant. One example of a dental implant has been discussed and is shown in FIG. 1. It is contemplated that other dental implants may be used instead of dental implant 110 shown in FIG. 1. A surface of the desired structure is exposed to oxygen to naturally form a native oxide layer thereon. After machining, at least a portion of the surface is immersed in a single solution of citric acid and HF acid to remove the native oxide and to produce surface irregularities having a peak-to-valley height less than about 10 microns and, more typically, less than about 5 microns or less than about 3 microns.

According to another method, a uniformly roughened surface on Ti 6/4 alloy for contact with living bone comprises (a) performing an initial treatment that removes substantially all of the native oxide from the surface of the Ti 6/4 alloy; and (b) after performing the initial treatment, exposing the Ti 6/4 alloy in an aqueous solution of citric acid and HF acid for a suitable time period to create the desired surface topography.

The initial treatment may include etching the surface with HF acid. According to another method, the initial treatment includes grit blasting to remove substantially all of the native oxide. The initial treatment as used in this process is used to remove aesthetic surface irregularities (e.g., tooling marks, minor galling) caused during the machining.

It is important to remove substantially all the native oxide from the implant surface (e.g., a dental implant-surface) that is intended to interface with the living bone, so that the subsequent treatment of that surface produces a substantially uniform surface texture to promote uniform bonding to the living bone. Thus, the native oxide layer is desirably removed from substantially all of the bone-interfacing surface of the implant.

In one method, the initial treatment includes exposing the Ti 6/4 alloy to HF acid for a time period of from about 45 seconds to a minute at ambient temperature. It is contemplated that the processing conditions of the initial treatment may vary. After this initial treatment, the Ti 6/4 alloy may be exposed to the aqueous solutions of citric acid and HF acid such as discussed above.

In one embodiment, the two step process of exposing the Ti 6/4 alloy results in a generally uniform roughened surface having irregularities with peak-to-valley heights of less than about 10 microns. More specifically, the generally uniform roughened surface has irregularities with peak-to-valley heights of less than about 5 or less than about 3 microns. In one embodiment, the generally uniform roughened surface generally has irregularities with peak-to-peak distances of from about 1 to about 3 microns. The irregularities may be cone-shaped elements and it is contemplated that such irregularities may be of different shapes. It is contemplated that the irregularities may be in the form of a substantially uniform array.

As with the one step process, the two step process using a Ti 6/4 alloy may be used on implant. One example of an implant is a dental implant such as shown in FIG. 1.

Another two step process comprises exposing the bone-interfacing portion to an initial treatment and then exposure to an aqueous solution of citric acid and HF acid for a suitable time period. The initial treatment removes substantially all of the native oxide from the Ti 6/4 alloy and forms a modified surface. The modified surface generally has irregularities with peak-to-valley heights of less than about 10 microns.

According to another method, the modified surface may be located only on a portion of the plurality of turns of the thread. In another method, the modified surface may be located only below a first turn of the plurality of turns that is adjacent to the gingival end. In yet another embodiment, the aqueous solution of citric acid and HF acid may be exposed to the gingival end.

Another method of preparing a dental implant involves using a blank of a Ti 6/4 alloy. The blank is machined to produce a desired structure of the dental implant. One example of a dental implant has been discussed and shown in FIG. 1. It is contemplated that other dental implants may be used instead of dental implant 110 shown in FIG. 1. A surface of the desired structure is exposed to oxygen to naturally form a native oxide layer thereon. After machining, at least a portion of the surface is exposed to an initial treatment and then is immersed in a aqueous solution of citric acid and HF acid to remove the native oxide and to produce surface irregularities having a peak-to-valley height less than about 10 microns and, more typically, less than about 5 microns or less than about 3 microns.

Titanium

Titanium has been generally used in implants such as, for example, dental implants. Commercially pure titanium typically includes trace amounts of carbon, iron, oxygen, hydrogen, and nitrogen. Types of commercial grade titanium that may be used in the processes of the present invention include commercial grade 3 or grade 4 titanium. It is contemplated that other grades of titanium may be used.

One desirable characteristic of titanium is the rapid formation of tenacious titanium oxide films on the surface, which contributes to titanium's resistance to corrosion. This oxide film is believed to be a combination of various oxides of titanium, including $TiO$, $TiO_2$, $Ti_2O_3$, and $Ti_3O_4$. This oxide film is referred to as "native oxide" film.

According to one method, a uniformly roughened surface may be obtained on titanium, which is to contact living bone. One method for obtaining such a uniform roughened surface may be performed in a single step. This method involves exposing titanium in an aqueous solution of citric acid and HF acid for a suitable time period to remove the native oxide from the titanium so as to expose the titanium metal surface and create the desired surface topography.

It is desirable to remove substantially all of the native oxide and even more desirable to remove all of the native oxide from the titanium during the exposure to the aqueous solution. It is understood by those of ordinary skill in the art, however, that some smaller bits of native oxide may still remain on the titanium alloy after exposure to the citric acid and HF acid. The method typically also includes rinsing the desired surface topography so as to remove the residual aqueous solution.

The aqueous solution generally comprises from about 1 to about 50 wt. % citric acid. More specifically, the aqueous solution may comprise from about 22 to about 23 wt. % citric acid. The citric acid may be the same as described above in connection with the Ti 6/4 alloy.

The aqueous solution generally comprises from about 0.01 to about 1.0 wt. % HF acid. More specifically, the aqueous solution comprises from about 0.07 to about 0.08 wt. % HF acid. Commercially available HF acid may be used in this processing.

The aqueous solution may also further include sulfuric acid. The aqueous solution may comprise from 0 to about 20 wt. % sulfuric acid ($H_2SO_4$). More specifically, the aqueous solution may comprise from about 5 to about 6 wt. % sulfuric acid. Commercially available sulfuric acid may be used in this invention.

The aqueous solution may comprise from about 1 to about 50 wt. % citric acid, 0 to about 20 wt. % sulfuric acid, and from about 0.01 to about 1.0 wt. % HF acid. More specifically, the aqueous solution comprises from about 22 to about 23 wt. % citric acid, from about 0.07 to about 0.09 wt. % HF acid, and from about 5 to about 6 wt. % sulfuric acid.

The processing conditions for exposing the titanium in the aqueous solution of citric acid and HF acid may vary. One non-limiting example of processing conditions for exposing the titanium in the aqueous solution of citric acid and HF acid is a temperature of from about 55 to about 80° C. for a time period of from about 7 to about 8 minutes. One specific example is a temperature of about 66° C. and a time period of from about 7 minutes and 30 seconds. It is contemplated that other temperatures and times may be used for exposing the aqueous solution of citric acid and HF acid to the titanium alloy.

In one embodiment, the one step process of exposing the titanium in an aqueous solution of citric acid and HF acid for a suitable time period results in a generally uniform roughened surface having irregularities with peak-to-valley heights of less than about 10 microns. More specifically, the roughened surface has irregularities with peak-to-valley heights of less than about 5 or less than about 3 microns. In one embodiment, the roughened surface generally has irregularities with peak-to-peak distances of from about 1 to about 3 microns. The irregularities may be cone-shaped elements and it is contemplated that such irregularities may be of different shapes. It is contemplated that the irregularities may be in the form of a substantially uniform array.

As discussed above, the method for preparing a uniformly roughened surface may be done on an implant (e.g., a dental implant), which is surgically implanted in living bone. One non-limiting example of a dental implant (a screw-type dental implant) is depicted in FIG. 1. It is contemplated that other implants, including other dental implants, may be used.

It is important to remove substantially all the native oxide from the implant surface (e.g., a dental implant surface) that is intended to interface with the living bone so that a substantially uniform surface texture is formed that promotes uniform bonding to the living bone. Thus, the native oxide layer is desirably removed from substantially all of the entire bone-interfacing surface of the implant.

One method comprises exposing the bone-interfacing portion to an aqueous solution of citric acid and HF acid for a suitable time period. The aqueous solution of citric acid and HF acid removes substantially all of the native oxide from the titanium and forms a modified surface. The modified surface generally has irregularities with peak-to-valley heights of less than about 10 microns.

According to another method, the modified surface may be located only on a portion of the plurality of turns of the thread. In another method, the modified surface may be located only below a first turn of the plurality of turns that is adjacent to the gingival end. In yet another embodiment, the aqueous solution of citric acid and HF acid may be exposed to the gingival end.

Another method of preparing a dental implant involves using a blank of titanium. The blank is machined to produce a desired structure of the dental implant. One example of a dental implant has been discussed and is shown in FIG. 1. It is contemplated that other dental implants may be used instead of the dental implant 110 shown in FIG. 1. A surface of the desired structure is exposed to oxygen to naturally form a native oxide layer thereon. After machining, at least a portion of the surface is immersed in a single solution of citric acid and HF acid to remove the native oxide and to produce surface irregularities having a peak-to-valley height less than about 10 microns and, more typically, less than about 5 microns or less than about 3 microns.

According to another method, a uniformly roughened surface on titanium for contact with living bone comprises (a) performing an initial treatment that removes substantially all of the native oxide from the surface of the titanium; and (b) after performing the initial treatment, exposing the titanium in an aqueous solution of citric acid and HF acid for a suitable time period to create the desired surface topography.

The initial treatment may include etching the surface with HF acid. According to another method, the initial treatment includes grit blasting to remove substantially all of the native oxide. The initial treatment as used in this process is used to remove aesthetic surface irregularities (e.g., tooling marks, minor galling) caused during the machining.

It is important to remove substantially all the native oxide from the implant surface (e.g., a dental implant surface) that is intended to interface with the living bone, so that the subsequent treatment of that surface produces a substantially uniform surface texture to promote uniform bonding to the living bone. Thus, the native oxide layer is desirably removed from substantially all of the entire bone-interfacing surface of the implant.

In one method, the initial treatment includes exposing the titanium to HF acid for a time period of from about 45 seconds to a minute at ambient temperature. It is contemplated that the processing conditions of the initial treatment may vary. After this initial treatment, the titanium may be exposed to the aqueous solutions of citric acid and HF acid such as discussed above.

In one embodiment, the two step process of exposing the titanium results in a generally uniform roughened surface having irregularities with peak-to-valley heights of less than about 10 microns. More specifically, the generally uniform roughened surface has irregularities with peak-to-valley heights of less than about 5 or less than about 3 microns. In one embodiment, the generally uniform roughened surface generally has irregularities with peak-to-peak distances of from about 1 to about 3 microns. The irregularities may be cone-shaped elements and it is contemplated that such irregularities may be of different shapes. It is contemplated that the irregularities may be in the form of a substantially uniform array.

As with the one step process, the two step process using titanium may be used on an implant. One example of an implant is a dental implant such as shown in FIG. 1.

Another two step process comprises exposing the bone-interfacing portion to an initial treatment and then exposure to an aqueous solution of citric acid and HF acid for a suitable time period. The initial treatment removes substantially all of the native oxide from the titanium and forms a modified surface. The modified surface generally has irregularities with peak-to-valley heights of less than about 10 microns.

According to another method, the modified surface may be located only on a portion of the plurality of turns of the thread. In another method, the modified surface may be located only below a first turn of the plurality of turns that is adjacent to the gingival end. In yet another embodiment, the aqueous solution of citric acid and HF acid may be exposed to the gingival end.

Another method of preparing a dental implant involves using a blank of titanium. The blank is machined to produce a desired structure of the dental implant. One example of a dental implant has been discussed and shown in FIG. 1. It is contemplated that other dental implants may be used instead of dental implant 110 shown in FIG. 1. A surface of the desired structure is exposed to oxygen to naturally form a native oxide layer thereon. After machining, at least a portion of the surface is exposed to an initial treatment and then is immersed in a aqueous solution of citric acid and HF acid to remove the native oxide and to produce surface irregularities having a peak-to-valley height less than about 10 microns and, more typically, less than about 5 microns or less than about 3 microns.

EXAMPLES

Example No. 1

An example of a screw-type cylindrical implant made of 6/4 titanium alloy E.L.I. (6 wt. % aluminum and 4 wt. % vanadium) is shown in FIGS. 2a-c.

The implant was exposed to an aqueous solution of 16.7 wt. % citric acid and 0.18 wt. % hydrofluoric (HF) acid with the remainder being water. The HF was 5% v/v HF (2.87% w/w). The aqueous solution was at a temperature of 30° C. The implant was exposed for 18 minutes and 30 seconds to remove the native oxide from the Ti 6/4 E.L.I. alloy. The implant was then rinsed to remove the residual acids from the surfaces of the implant. One of the rinses included using water that was heated to a temperature of at least 65° C.

Figure 2A:
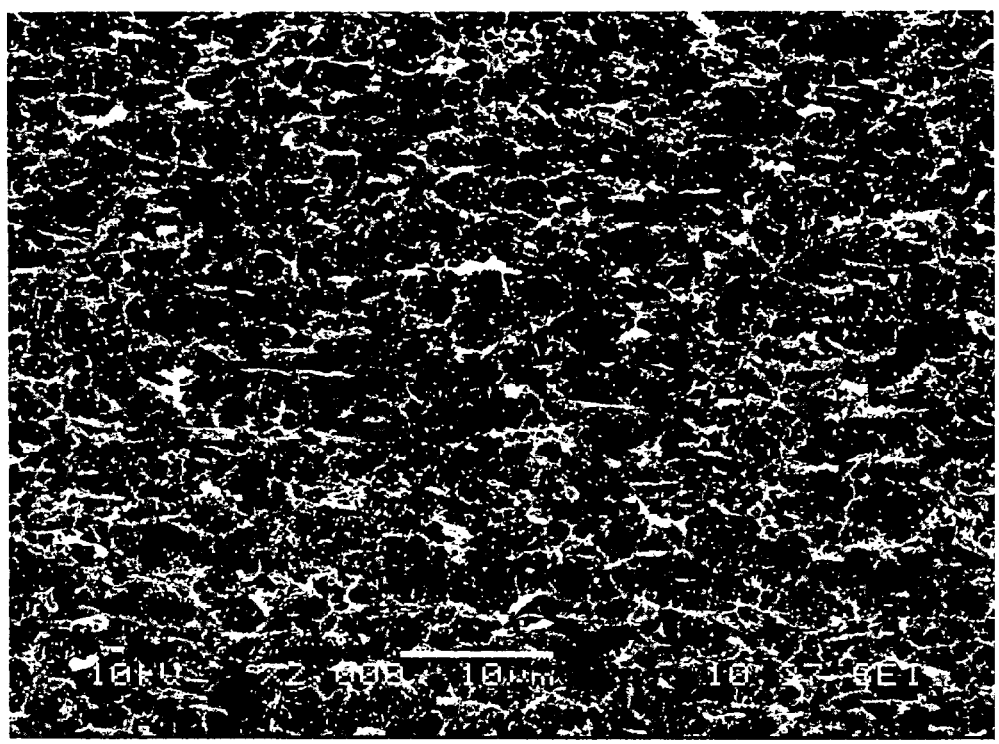
FIGS. 2a-d are surfaces of a Ti 6/4 alloy dental implant after being exposed by a one step process using citric acid.
Figure 2B:
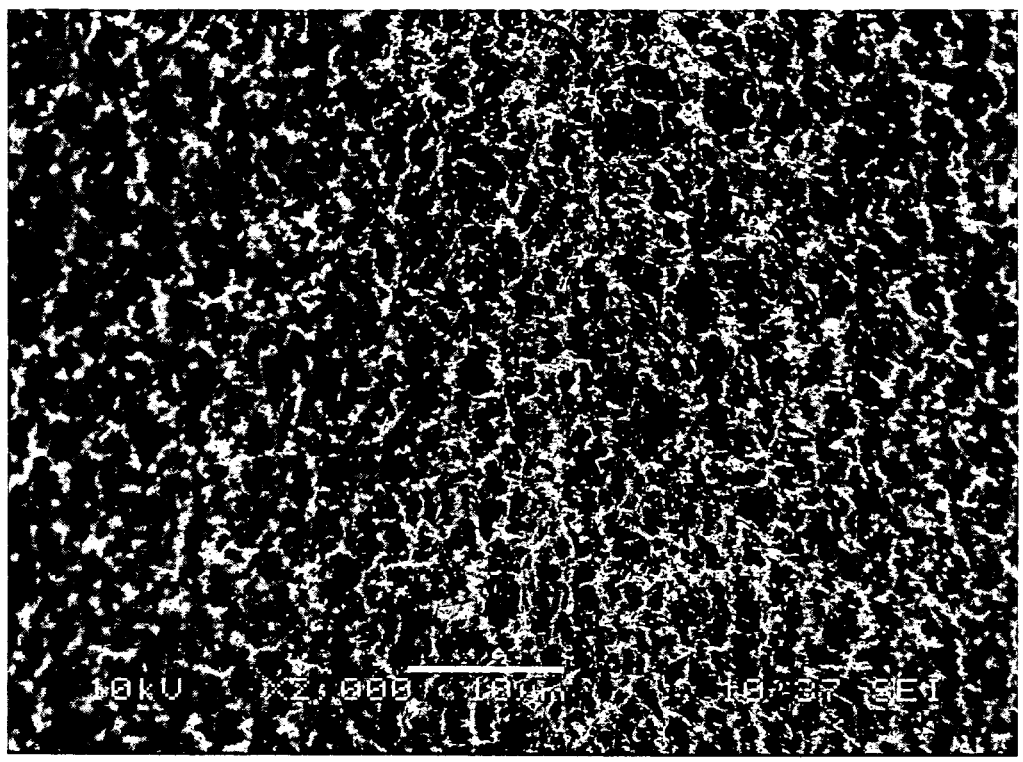
Figure 2C:
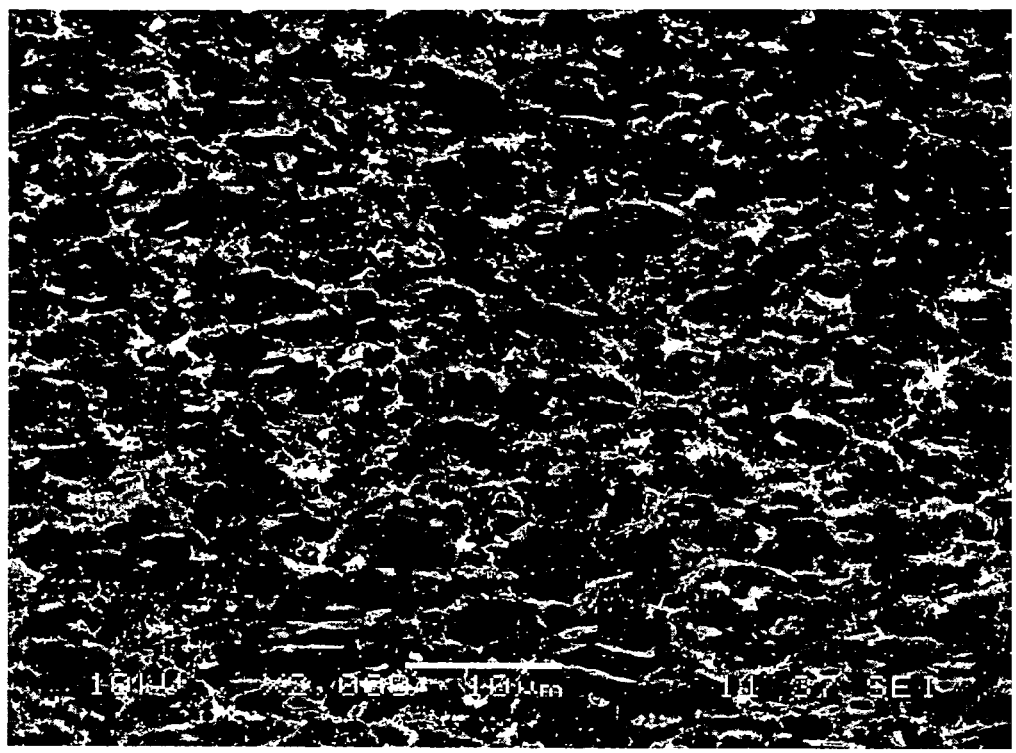
Figure 2D:
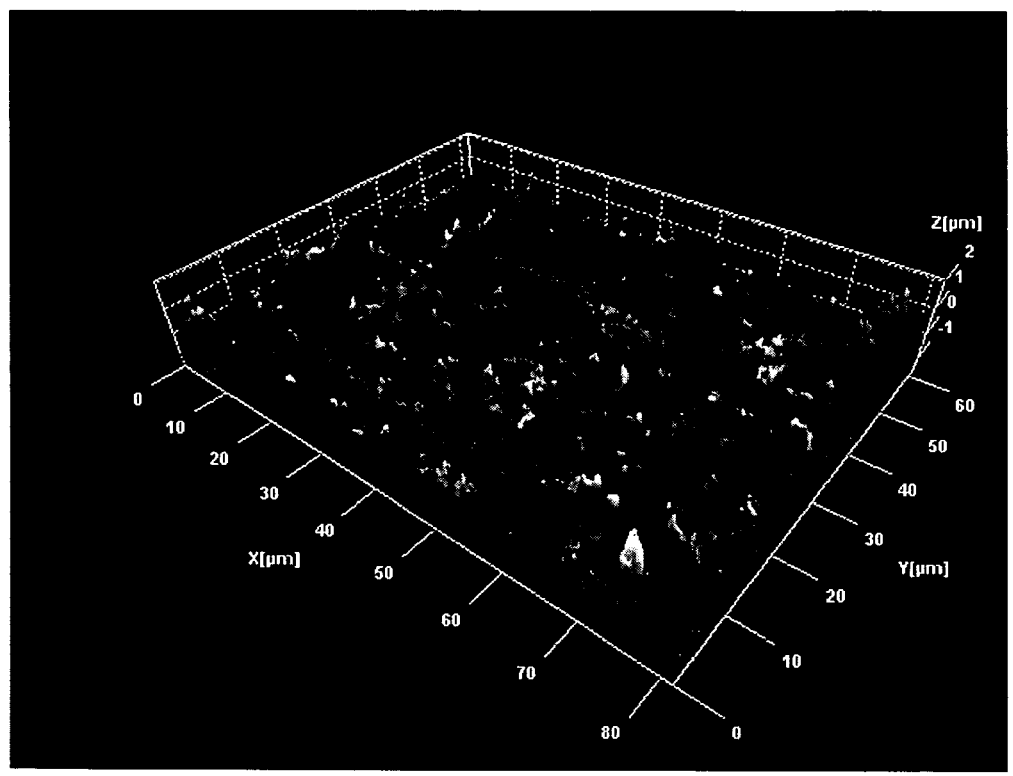

After this processing, SEMs of the implant were taken and are shown in FIGS. 2a-c. FIG. 2a is an SEM (scanning electron microscopy) photograph that shows a minor diameter of a thread of the implant at a magnification of 2,000. FIG. 2b is an SEM photograph that shows a flank of the thread of the implant at a magnification of 2,000. FIG. 2c is an SEM photograph that shows a flute of the thread of the implant at a magnification of 2,000. FIG. 2d is a photograph of the implant using an interferometric surface profiler. It will be observed that the surface features over the areas shown are generally consistent and generally uniform, and resulted in an Osseotite® surface. The highest peak-to-valley measured on FIG. 2d was 3.5 microns.

Example No. 2

An example of a screw-type cylindrical implant made of 6/4 titanium alloy E.L.I. (6 wt. % aluminum and 4 wt. % vanadium) is shown in FIGS. 3a-c.

In the first step, the implant was exposed to a 4.28 wt. % HF solution with the remainder being water. The HF was 50 ml of 15% v/v (8.44% w/w). The HF solution was at a temperature of 25° C. The implant was exposed to the HF solution for about 52 seconds and then rinsed with water.

In the second step, the implant was exposed to an aqueous solution of 16.7 wt. % citric acid and 0.18 wt. % HF acid with the remainder being water. The HF was 5% v/v HF (2.87% w/w). The aqueous solution was at a temperature of 30° C. The implant was exposed for 18 minutes and 30 seconds to remove the native oxide from the Ti 6/4 E.L.I. alloy. The implant was then rinsed to remove the residual acids from the surfaces of the implant. One of the rinses included using water that was heated to a temperature of at least 65° C.

Figure 3A:
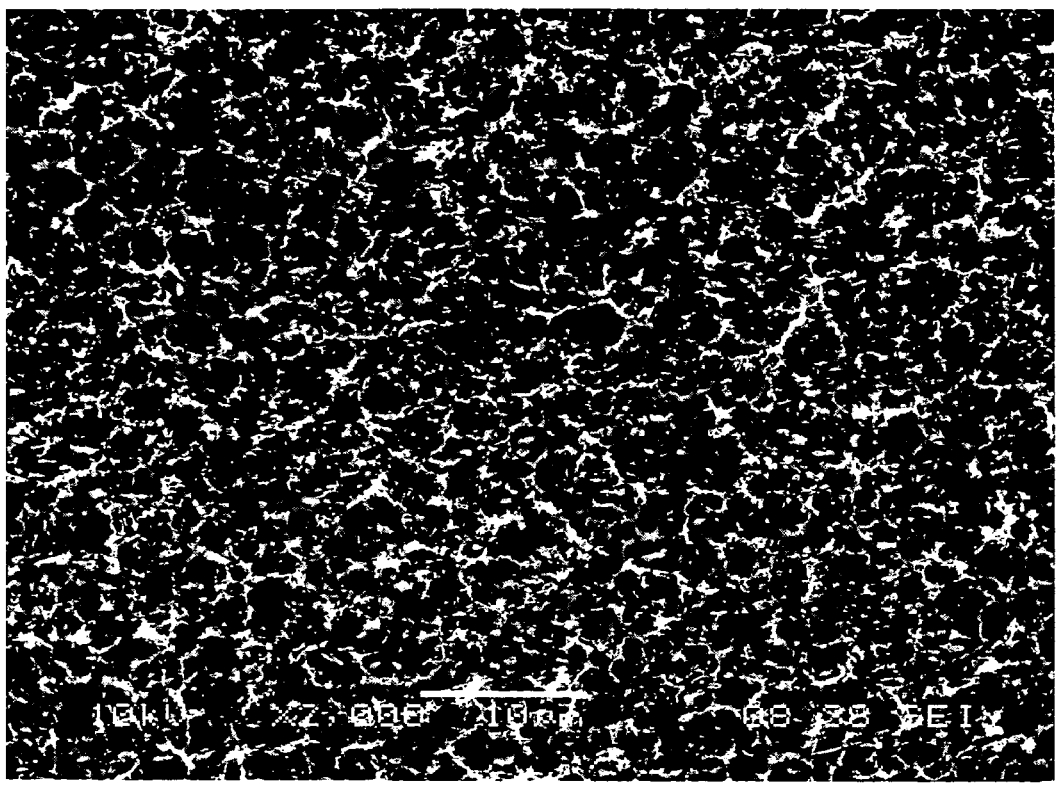
FIGS. 3a-d are surfaces of a Ti 6/4 alloy dental implant after being exposed by a two step process using citric acid.
Figure 3B:
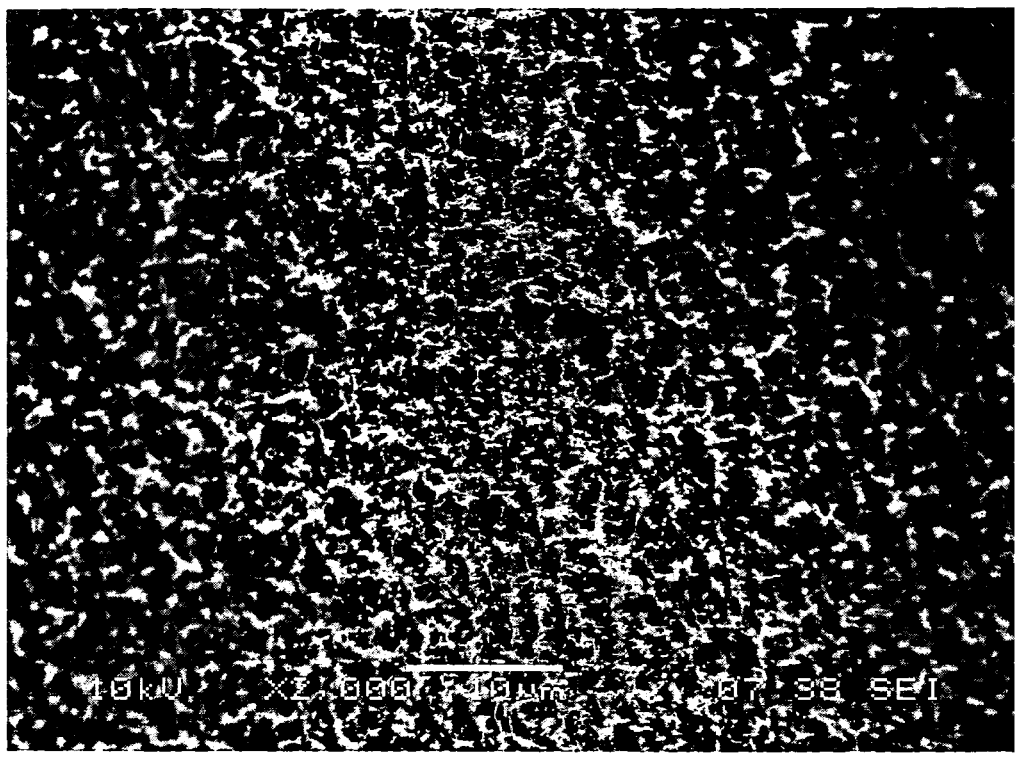
Figure 3C:
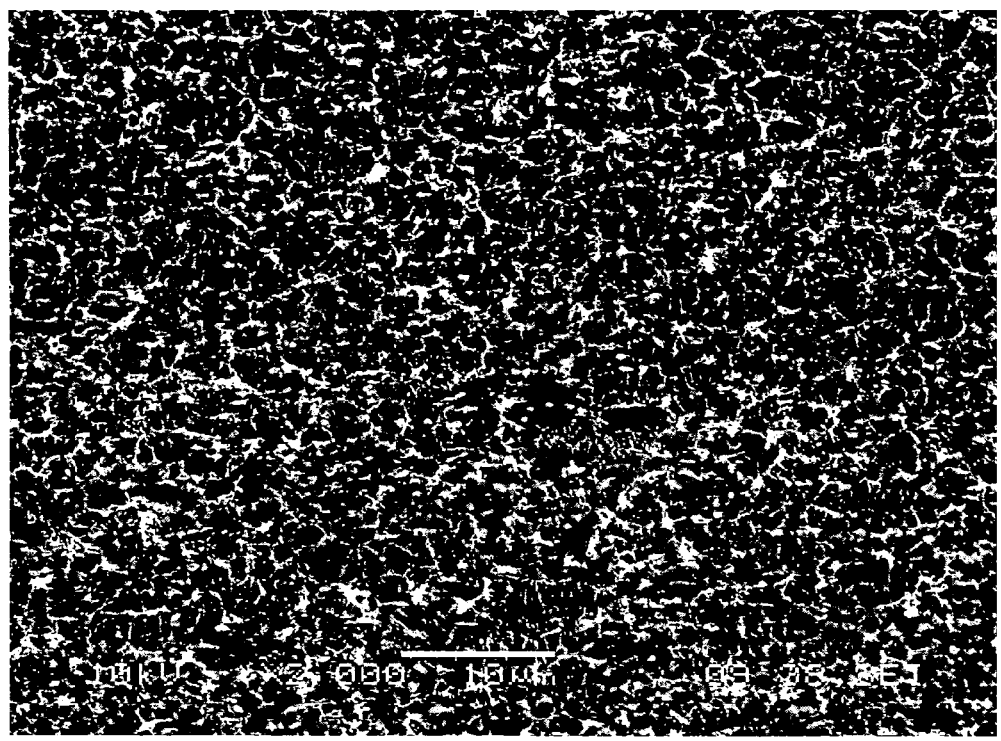
Figure 3D:
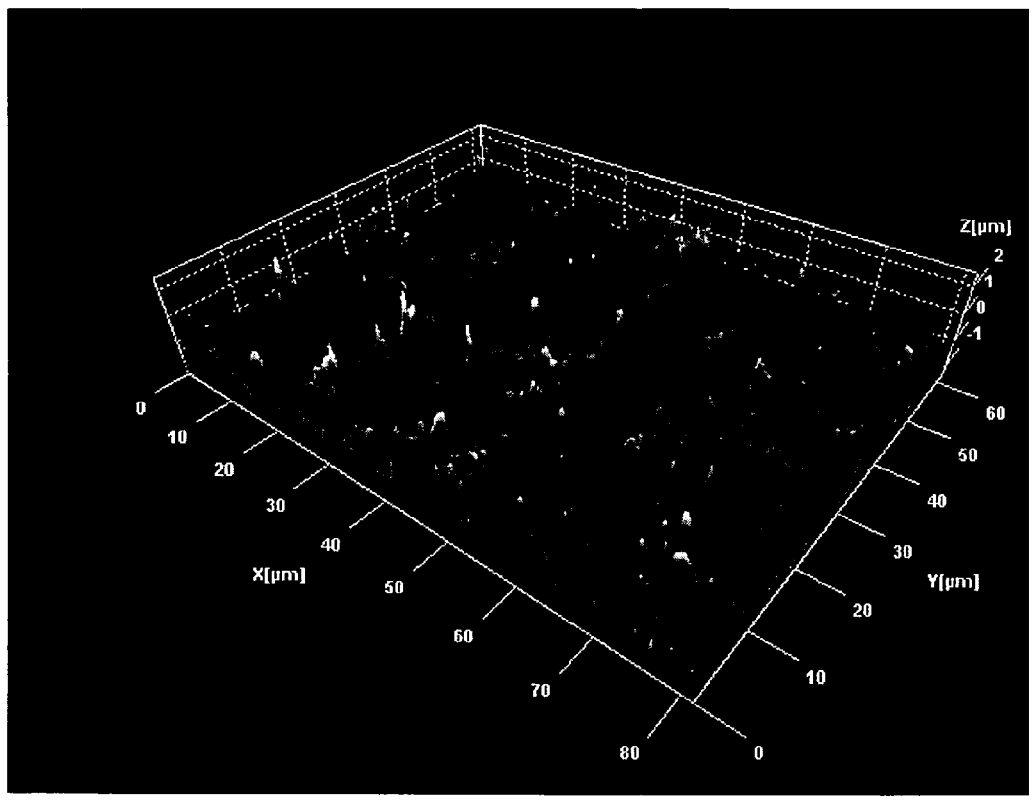

After this processing, SEMs of the implant were taken and are shown in FIGS. 3a-c. FIG. 3a is an SEM photograph that shows a minor diameter of a thread of the implant at a magnification of 2,000. FIG. 3b is an SEM photograph that shows a flank of the thread of the implant at a magnification of 2,000. FIG. 3c is an SEM photograph that shows a flute of the thread of the implant at a magnification of 2,000. FIG. 3d is a photograph of the implant using an interferometric surface profiler. It will be observed that the surface features over the areas shown are generally consistent and generally uniform, and resulted in an Osseotite® surface. The highest peak-to-valley measured on FIG. 3d was 3.81 microns.

Example No. 3

Figure 4A:
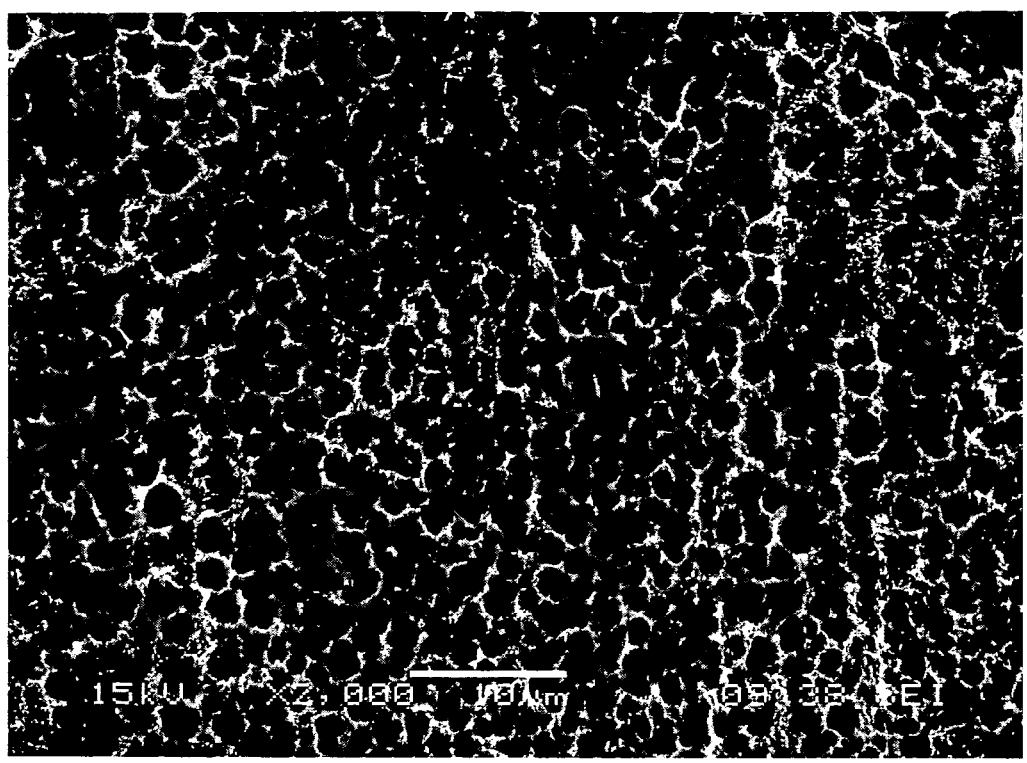
FIGS. 4a-d are surfaces of a grade 3 titanium dental implant after being exposed by a one step process using citric acid.
Figure 4B:
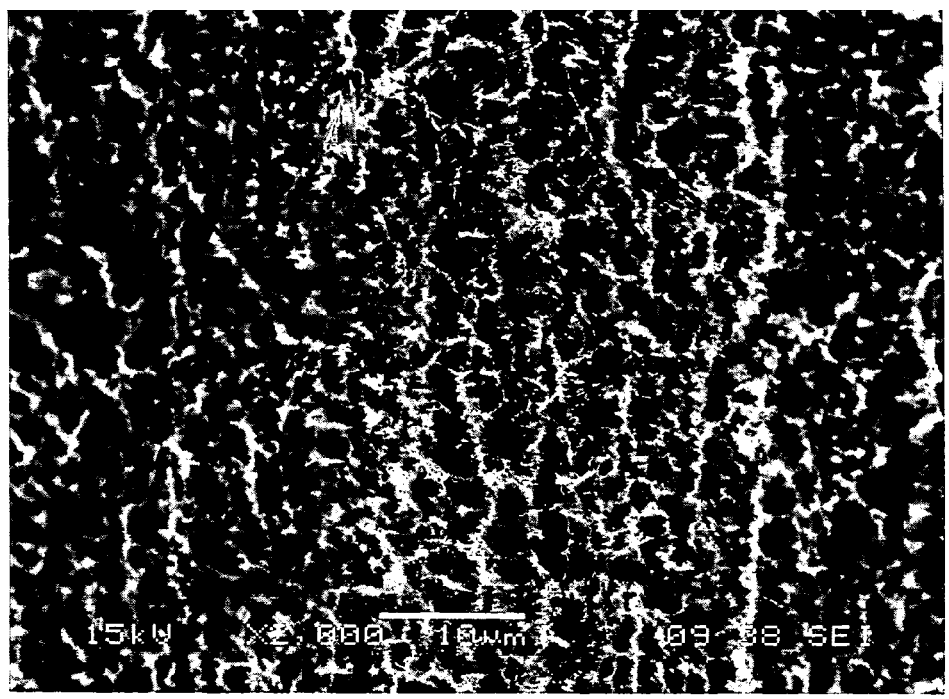
Figure 4C:
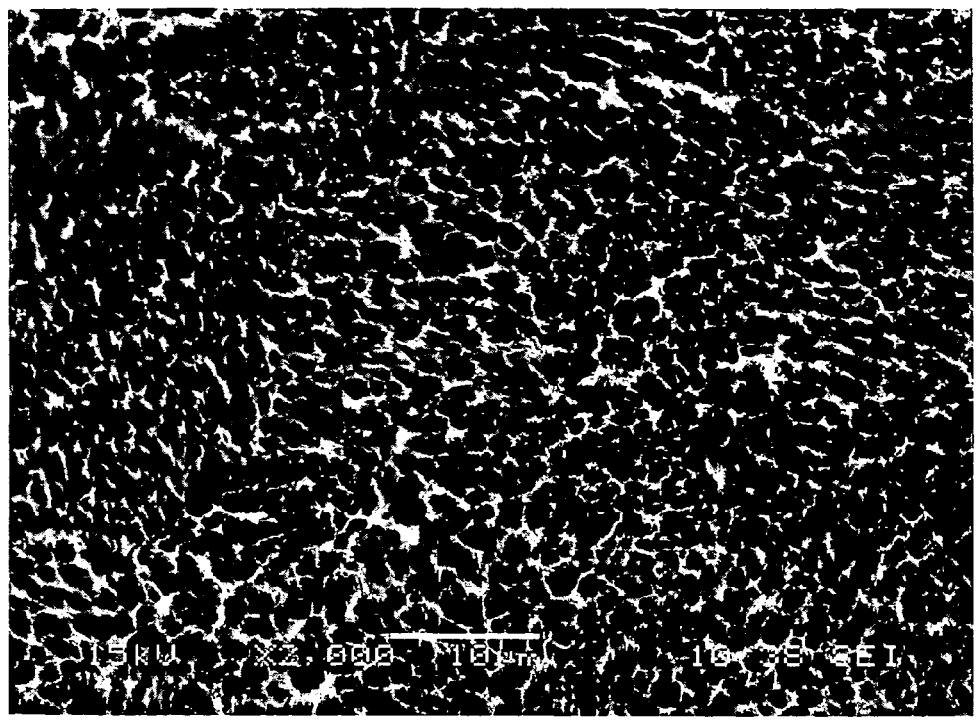

An example of a screw-type cylindrical implant made of grade 3 titanium is shown in FIGS. 4a-c.

The implant was exposed to an aqueous solution of 22.4 wt. % citric acid, 0.08 wt. % HF acid, and 5.58 wt. % sulfuric acid with the remainder being water. The HF was 5% v/v (2.87% w/w). The sulfuric acid was 4.4% v/v (7.45% w/w). The aqueous solution was at a temperature of 66° C. The implant was exposed for 7 minutes and 30 seconds to remove the native oxide from the grade 3 Ti implant. The implant was then rinsed to remove the residual acids from the surfaces of the implant. One of the rinses included using water that was heated to a temperature of at least 65° C.

Figure 4D:
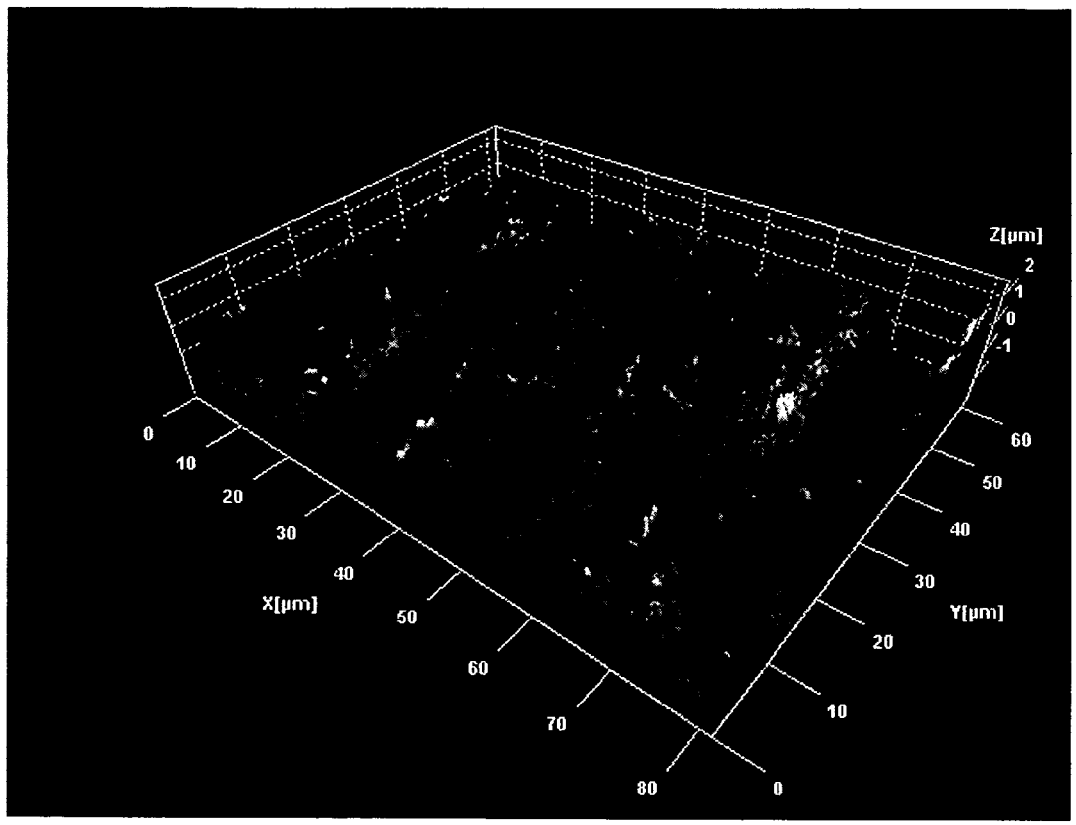

After this processing, SEMs of the implant were taken and are shown in FIGS. 4a-c. FIG. 4a is an SEM photograph that shows a minor diameter of a thread of the implant at a magnification of 2,000. FIG. 4b is an SEM photograph that shows a flank of the thread of the implant at a magnification of 2,000. FIG. 4c is an SEM photograph that shows a flute of the thread of the implant at a magnification of 2,000. FIG. 4d is a photograph of the implant using an interferometric surface profiler. As shown in FIGS. 4a-d, the surface features over the areas shown were generally consistent and generally uniform, and resulted in an Osseotite® surface. The highest peak-to-valley measured on FIG. 4d was 4.38 microns.

Example No. 4

Figure 5A:
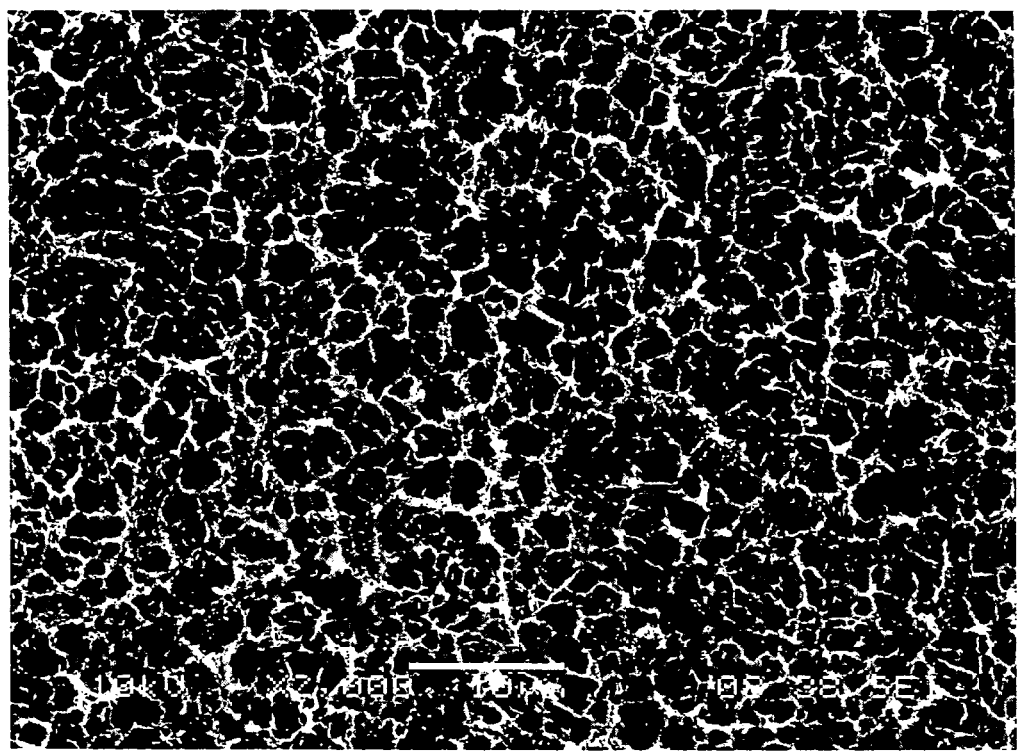
FIGS. 5a-d are surfaces of a grade 4 titanium dental implant after being exposed by a one step process using citric acid.
Figure 5B:
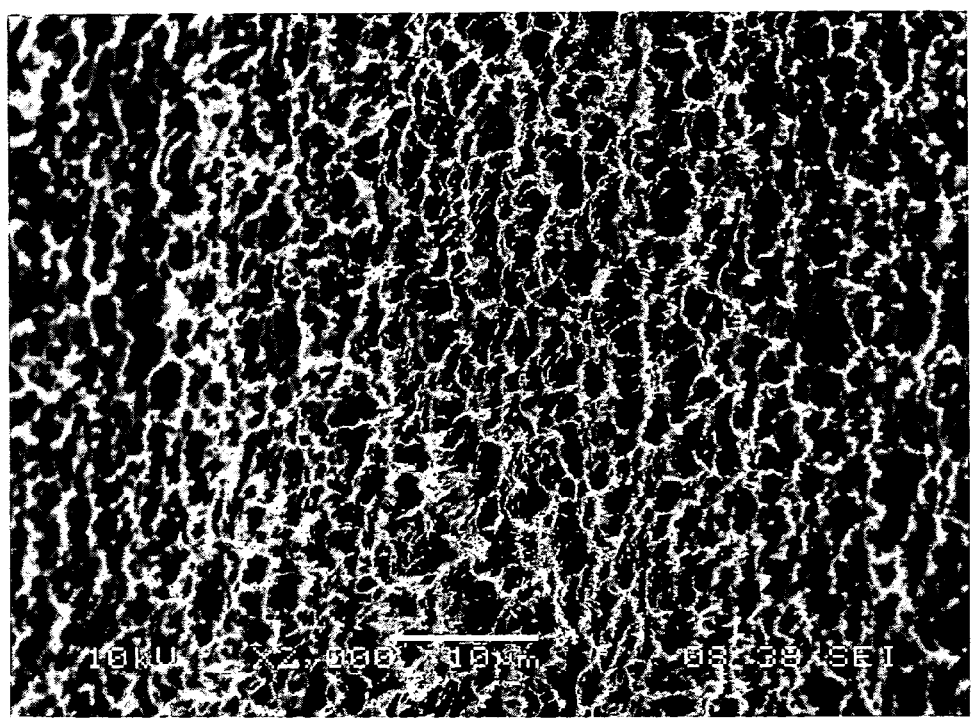
Figure 5C:
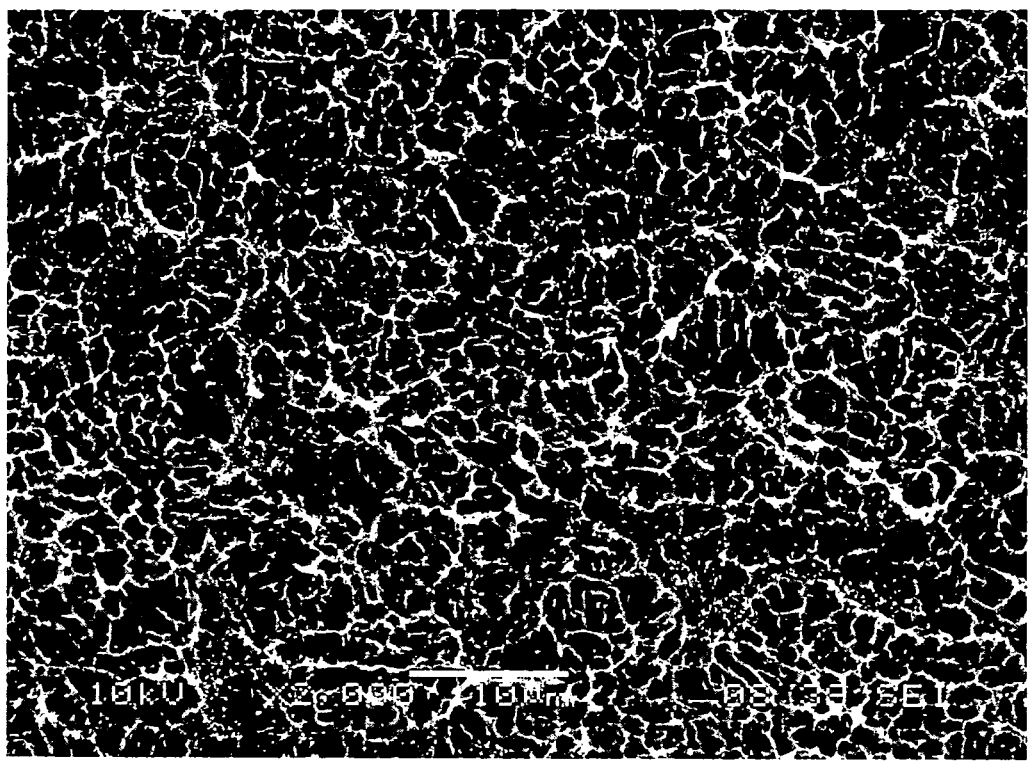

An example of a screw-type cylindrical implant made of grade 4 titanium is shown in FIGS. 5a-c.

The implant was exposed to an aqueous solution of 22.4 wt. % citric acid, 0.08 wt. % HF acid and 5.58 wt. % sulfuric acid with the remainder being water. The HF was 5% v/v (2.87% w/w). The sulfuric acid was 4.4% v/v (7.45% w/w). The aqueous solution was at a temperature of 66° C. The implant was exposed for 7 minutes and 30 seconds to remove the native oxide from the grade 4 Ti implant. The implant was then rinsed to remove the residual acids from the surfaces of the implant. One of the rinses included using water that was heated to a temperature of at least 65° C.

Figure 5D:
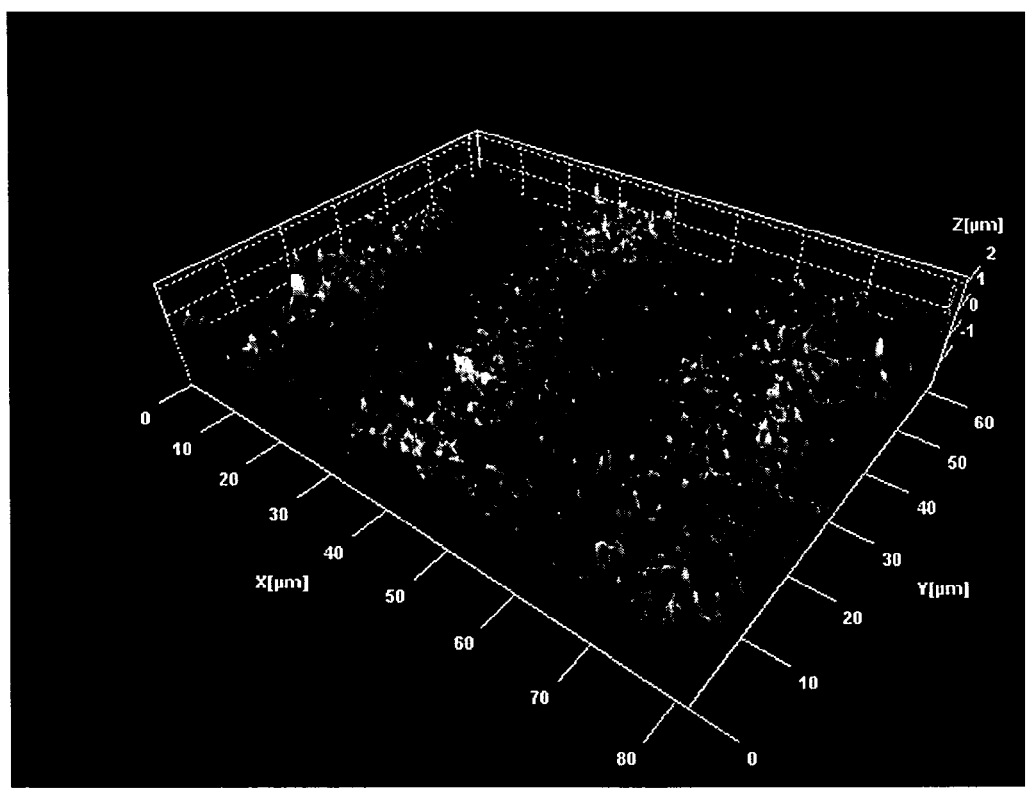

After this processing, SEMs of the implant were taken and are shown in FIGS. 5a-c. FIG. 5a is an SEM photograph that shows a minor diameter of a thread of the implant at a magnification of 2,000. FIG. 5b is an SEM photograph that shows a flank of the thread of the implant at a magnification of 2,000. FIG. 5c is an SEM photograph that shows a flute of the thread of the implant at a magnification of 2,000. FIG. 5d is a photograph of the implant using an interferometric surface profiler. As shown in FIGS. 5a-d, the surface features over the areas shown were generally consistent and generally uniform, and resulted in an Osseotite® surface. The highest peak-to-valley measured on FIG. 5d was 4.44 microns.

Example No. 5

Figure 6A:
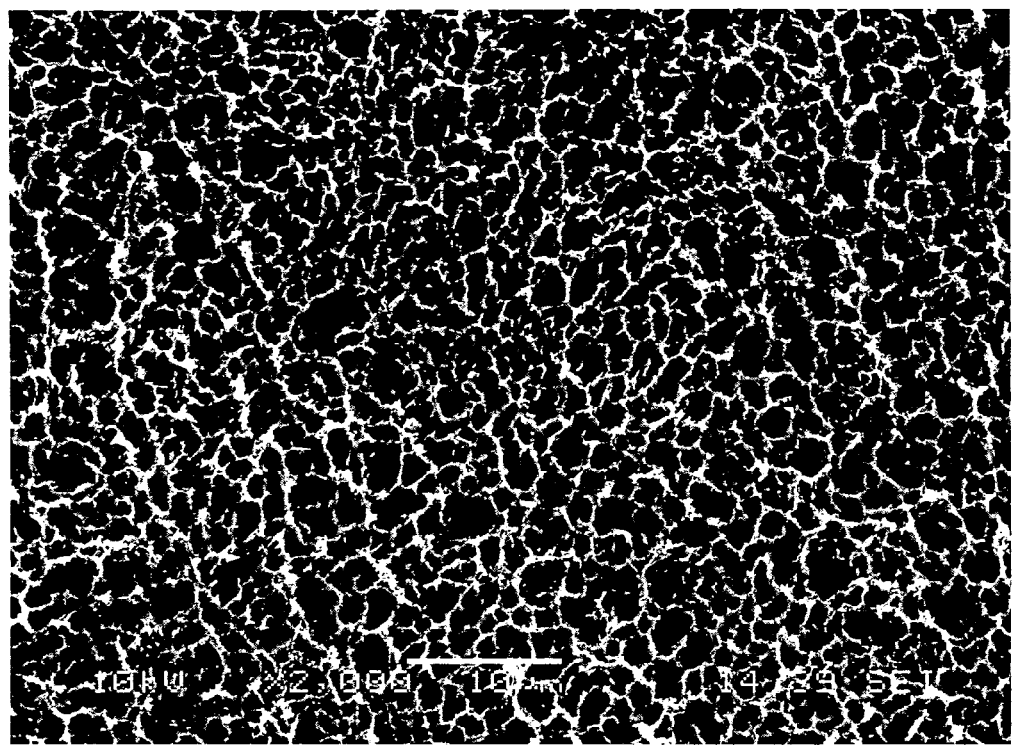
FIGS. 6a-d are surfaces of a grade 3 titanium dental implant after being exposed by a two step process using citric acid.
Figure 6B:
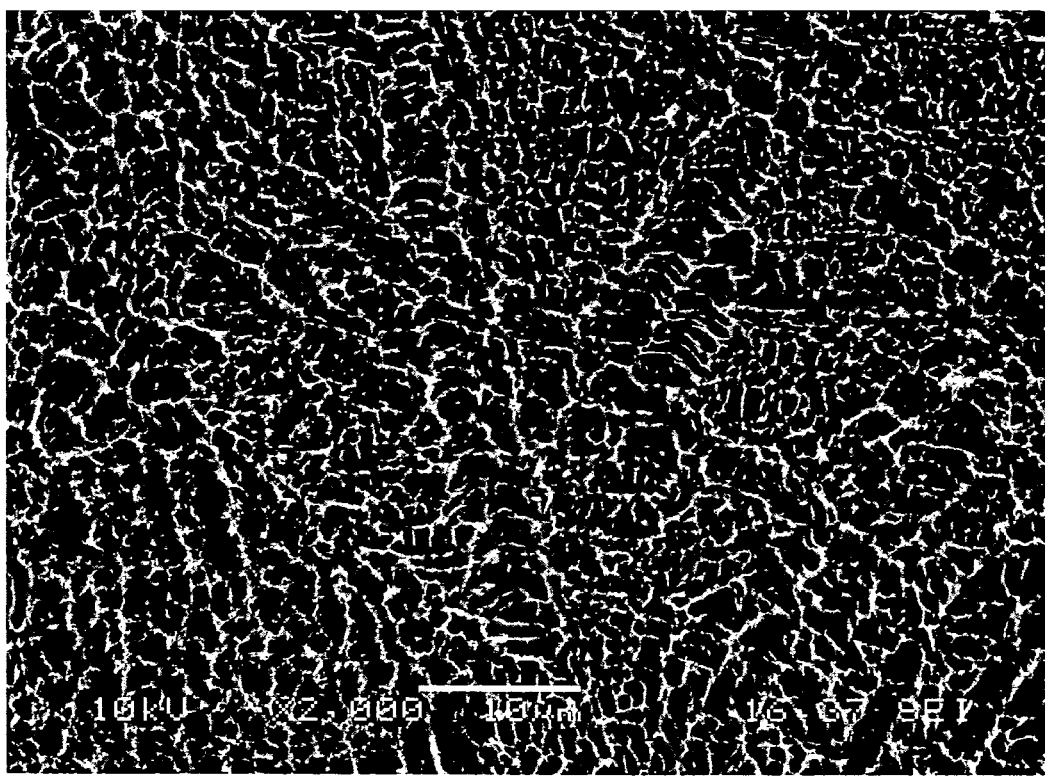
Figure 6C:
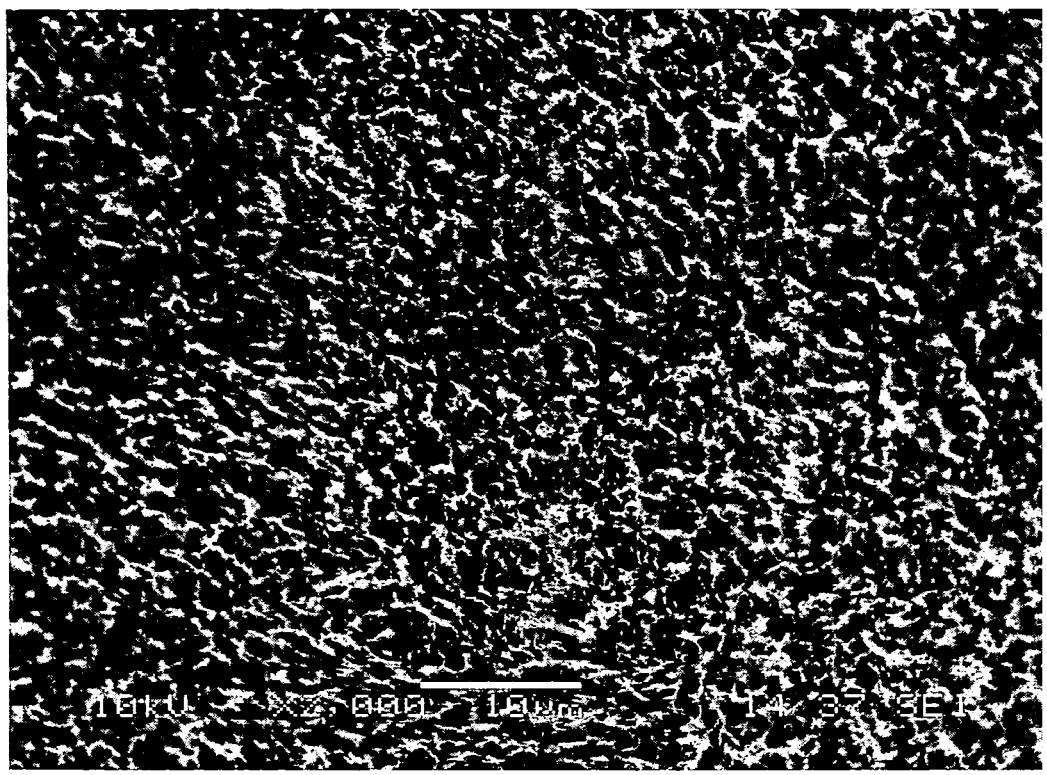

An example of a screw-type cylindrical implant made of grade 3 titanium is shown in FIGS. 6a-c.

In the first step, the implant was exposed to a 4.28 wt. % HF solution with the remainder being water. The HF was 50 ml of 15% v/v (8.44% w/w). The HF solution was at a temperature of 25° C. The implant was exposed to the HF solution for about 52 seconds and then rinsed with water.

In the second step, the implant was exposed to an aqueous solution of 22.4 wt. % citric acid, 0.08 wt. % HF acid, and 5.58 wt. % sulfuiric acid with the remainder being water. The HF was 5% v/v (2.87% w/w). The sulfuric acid was 4.4% v/v (7.45% w/w). The aqueous solution was at a temperature of 66° C. The implant was exposed for 7 minutes and 30 seconds to remove the native oxide from the grade 3 Ti implant. The implant was then rinsed to remove the residual acids from the surfaces of the implant. One of the rinses included using water that was heated to a temperature of at least 65° C.

Figure 6D:
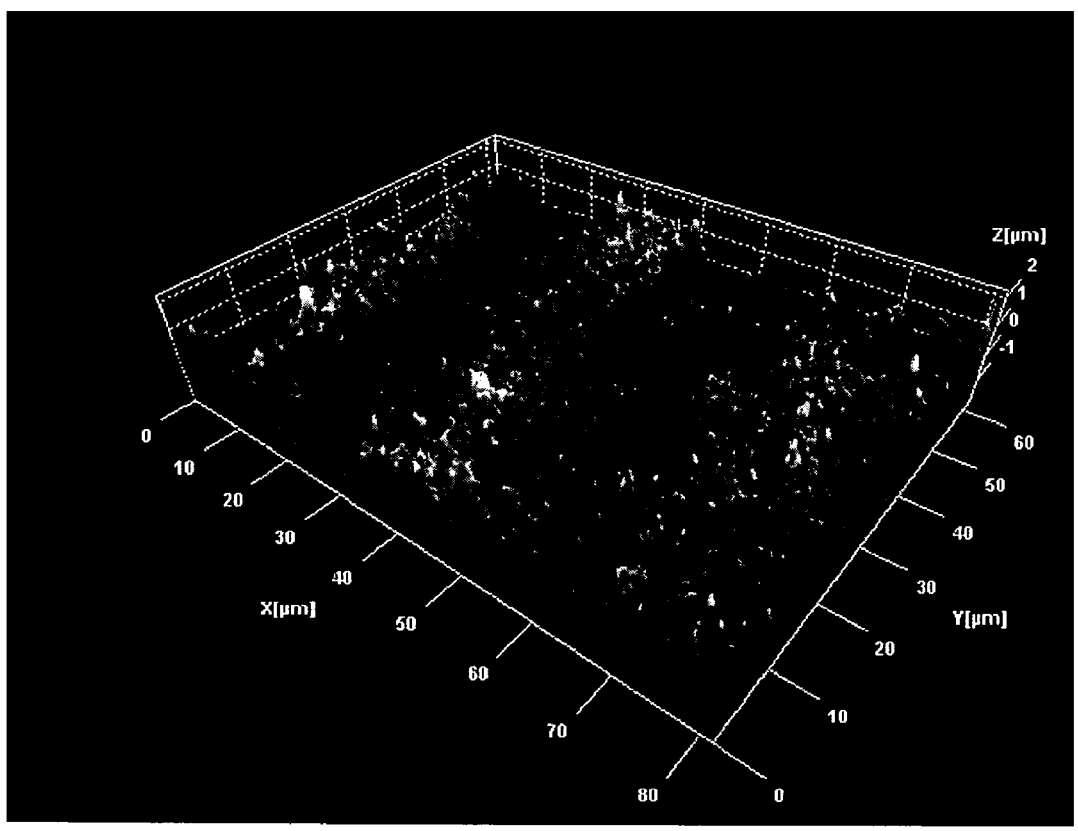

After this processing, SEMs of the implant were taken and are shown in FIGS. 6a-c. FIG. 6a is an SEM photograph that shows a minor diameter of a thread of the implant at a magnification of 2,000. FIG. 6b is an SEM photograph that shows a flank of the thread of the implant at a magnification of 2,000. FIG. 6c is an SEM photograph that shows a flute of the thread of the implant at a magnification of 2,000. FIG. 6d is a photograph of the implant using an interferometric surface profiler. As shown in FIGS. 6a-d, the surface features over the areas shown were generally consistent and generally uniform, and resulted in an Osseotite® surface. The highest peak-to-valley measured on FIG. 6d was 4.05 microns.

Example No. 6

Figure 7A:
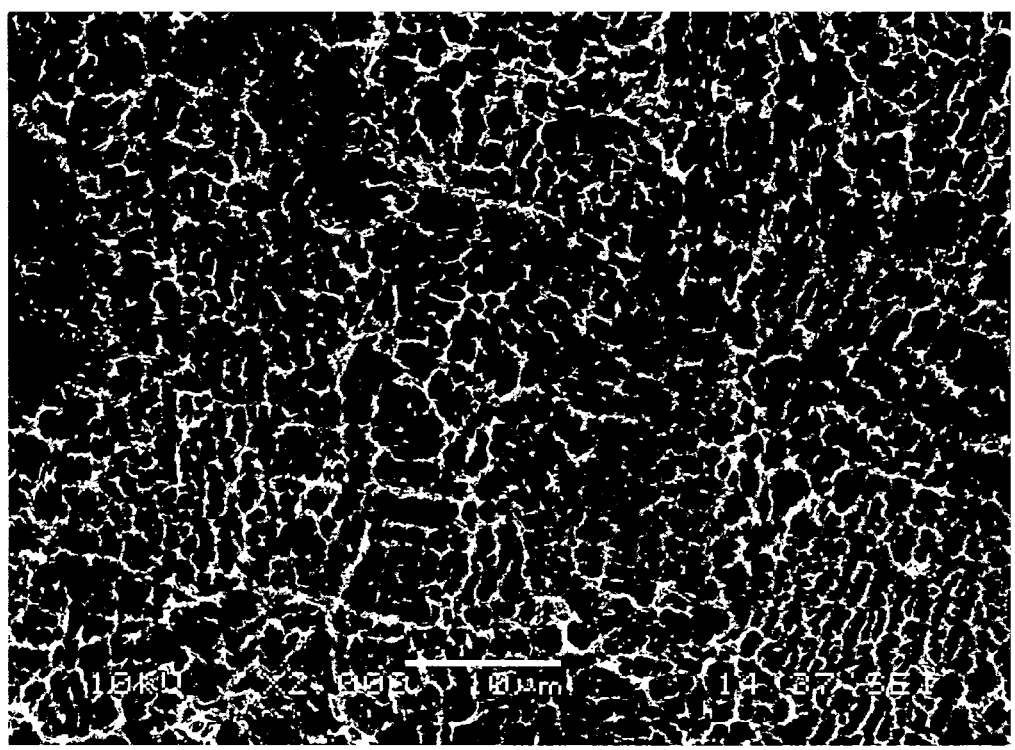
FIGS. 7a-d are surfaces of a grade 4 titanium dental implant after being exposed by a two step process using citric acid.
Figure 7B:
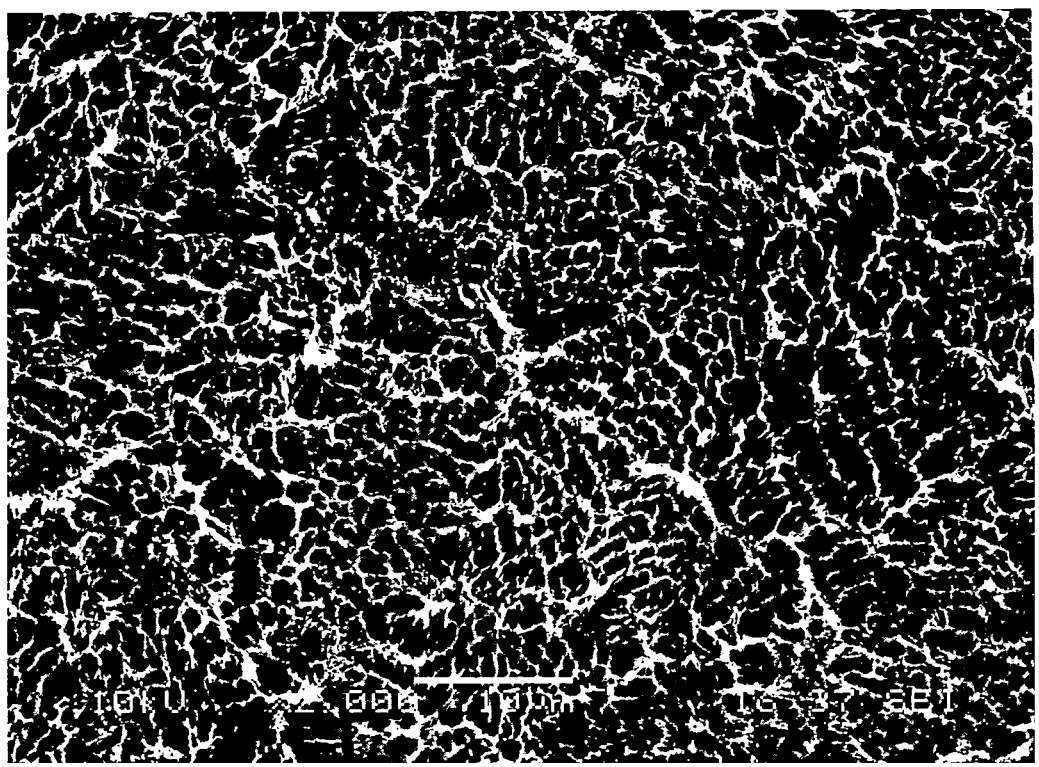
Figure 7C:
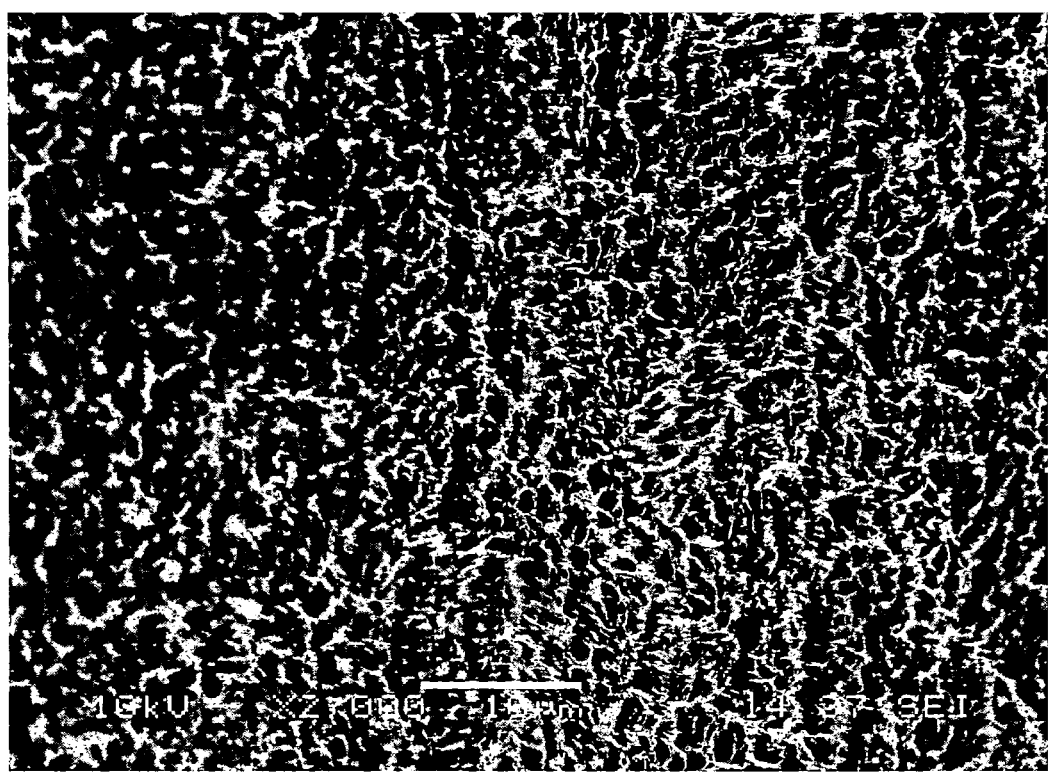

An example of a screw-type cylindrical implant made of grade 4 titanium is shown in FIGS. 7a-c.

In the first step, the implant was exposed to a 4.28 wt. % HF solution with the remainder being water. The HF was 50 ml of 15% v/v (8.44% w/w). The HF solution was at a temperature of 25° C. The implant was exposed to the HF solution for about 52 seconds and then rinsed with water.

In the second step, the implant was exposed to an aqueous solution of 22.4 wt. % citric acid, 0.08 wt. % HF acid and 5.58 wt. % sulfuric acid with the remainder being water. The HF was 5% v/v (2.87% w/w). The sulfuric acid was 4.4% v/v (7.45% w/w). The aqueous solution was at a temperature of 66° C. The implant was exposed for 7 minutes and 30 seconds to remove the native oxide from the grade 4 Ti implant. The implant was then rinsed to remove the residual acids from the surfaces of the implant. One of the rinses included using water that was heated to a temperature of at least 65° C.

Figure 7D:
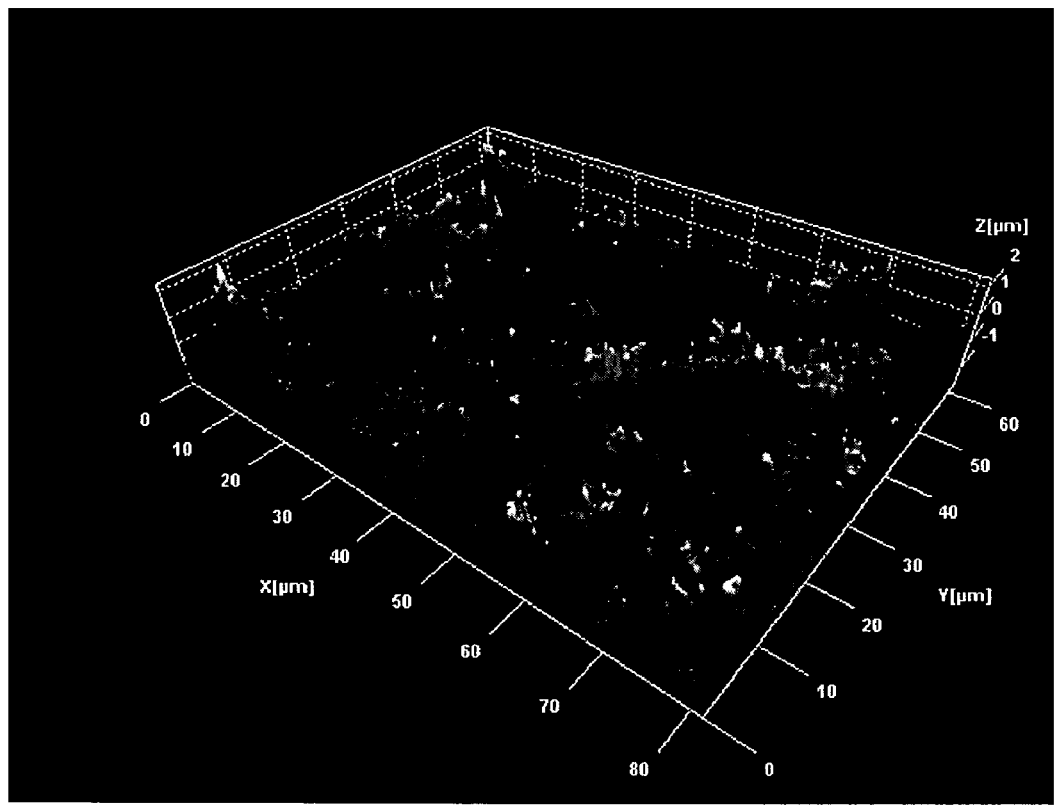

After this processing, SEMs of the implant were taken and are shown in FIGS. 7a-c. FIG. 7a is an SEM photograph that shows a minor diameter of a thread of the implant at a magnification of 2,000. FIG. 7b is an SEM photograph that shows a flank of the thread of the implant at a magnification of 2,000. FIG. 7c is an SEM photograph that shows a flute of the thread of the implant at a magnification of 2,000. FIG. 7d is a photograph of the implant using an interferometric surface profiler. As shown in FIGS. 7a-d, the surface features over the areas shown were generally consistent and generally uniform, and resulted in an Osseotite® surface. The highest peak-to-valley measured on FIG. 7d was 3.88 microns.

What is claimed is:

1. A method of producing a generally uniformly roughened surface on Ti 6/4 alloy for contact with living bone comprising the act of exposing the Ti 6/4 alloy in an aqueous solution of citric acid and hydrofluoric acid for a suitable time period to remove the native oxide from the Ti 6/4 alloy so as to expose the Ti 6/4 metal surface and create the desired surface topography, the aqueous solution comprises from about 1 to about 50 wt. % citric acid.

2. The method of claim 1 further including rinsing the desired surface topography so as to remove the residual aqueous solution.

3. The method of claim 1 wherein the aqueous solution comprises from about 16.0 to about 17.3 wt. % citric acid.

4. The method of claim 1 wherein the aqueous solution comprises from about 0.1 to about 1.0 wt. % hydrofluoric acid.

5. The method of claim 4 wherein the aqueous solution comprises from about 0.16 to about 0.20 wt. % hydrofluoric acid.

6. The method of claim 1 wherein the aqueous solution comprises from about 16 to about 17.3 wt. % citric acid and from about 0.16 to about 0.20 wt. % hydrofluoric acid.

7. The method of claim 1 wherein all of the native oxide is removed from the Ti 6/4 alloy.

8. The method of claim 1 wherein the Ti 6/4 alloy is a Ti 6/4 E.L.I. alloy.

9. The method of claim 1 wherein the method of producing a generally uniformly roughened surface on Ti 6/4 alloy for contact with living bone includes no additional acts.

10. A method of producing a generally uniformly roughened surface on Ti 6/4 alloy for contact with living bone comprising the act of exposing the Ti 6/4 alloy to an aqueous solution of citric acid and hydrofluoric acid for a suitable time period to remove the native oxide from the Ti 6/4 alloy so as to expose the Ti 6/4 metal surface and etch the exposed metal to achieve a roughened surface having irregularities with peak-to-valley heights of less than about 10 microns.

11. The method of claim 10 wherein the roughened surface has irregularities with peak-to-peak distances of from about 1 to about 3 microns.

12. The method of claim 11 wherein the roughened surface has irregularities with peak-to-valley heights of less than about 3 microns.

13. The method of claim 10 wherein the roughened surface has irregularities with peak-to-valley heights of less than about 5 microns.

14. A method of preparing a surface of a Ti 6/4 alloy implant that is surgically implantable in living bone, the surface having a native oxide layer thereon, the method comprising the act of:

exposing the Ti 6/4 alloy to an aqueous solution of citric acid and hydrofluoric acid for a suitable time period, wherein the aqueous solution of citric acid and hydrofluoric acid removes substantially all of the native oxide from the Ti 6/4 alloy and forms a modified surface with substantially uniform array of irregularities having peak-to-valley heights less than about 10 microns.

15. The method of claim 14 wherein the substantially uniform array of irregularities has peak-to-peak distances of from about 1 to about 3 microns.

16. The method of claim 14 wherein the substantially uniform array of irregularities has peak-to-valley heights of less than about 5 microns.

17. The method of claim 14 wherein the aqueous solution comprises from about 16.0 to about 17.3 wt. % citric acid.

18. A method of preparing a surface of a Ti 6/4 alloy implant that is surgically implantable in living bone, the surface having a native oxide layer thereon, the method comprising the acts of:

performing an initial treatment that removes substantially all of the native oxide from the surface of the Ti 6/4 alloy; and after performing the initial treatment, exposing the Ti 6/4 alloy to an aqueous solution of citric acid and hydrofluoric acid for a suitable time period to achieve a roughened surface having irregularities with peak-to-valley heights of less than about 10 microns.

19. A method of producing a generally uniformly roughened surface on titanium for contact with living bone comprising the act of exposing the titanium in an aqueous solution of citric acid and hydrofluoric acid for a suitable time period to remove the native oxide from the titanium so as to expose the titanium metal surface and create the desired surface topography, the aqueous solution comprises from about 1 to about 50 wt. % citric acid.

20. The method of claim 19 wherein the aqueous solution comprises from about 22 to about 23 wt. % citric acid.

* * * * *